United States Patent [19]

Hager et al.

[11] Patent Number: 5,366,897
[45] Date of Patent: Nov. 22, 1994

[54] METHOD FOR CONTROLLING THE CONVERSION OF IRON-CONTAINING REACTOR FEED INTO IRON CARBIDE

[75] Inventors: John P. Hager, Golden; Frank A. Stephens, Arvada; Frank M. Stephens, Jr., Lakewood, all of Colo.

[73] Assignee: Iron Carbide Holdings, Ltd., Lakewood, Colo.

[21] Appl. No.: 9,859

[22] Filed: Jan. 27, 1993

Related U.S. Application Data

[63] Continuation-in-part of Ser. No. 561,100, Aug. 1, 1990, abandoned.

[51] Int. Cl.$^5$ .......................... C22B 5/14; C01B 31/30
[52] U.S. Cl. .......................... 436/55; 75/376; 75/444; 75/446; 75/450; 75/451; 75/507; 423/439
[58] Field of Search .................. 75/376, 444, 450, 507, 75/451, 446; 423/439; 436/55; 422/62

[56] References Cited

U.S. PATENT DOCUMENTS

| | | | |
|---|---|---|---|
| 2,535,042 | 12/1950 | Cohn et al. | 23/208 |
| 2,752,234 | 6/1956 | Shipley | 75/26 |
| 2,780,537 | 2/1957 | Stelling et al. | 75/26 |
| 2,864,688 | 12/1958 | Reed | 75/26 |
| 2,894,831 | 7/1959 | Old et al. | 75/13 |
| 2,900,246 | 8/1959 | Keith et al. | 75/26 |
| 2,921,848 | 1/1960 | Agarwal | 75/26 |
| 3,021,208 | 2/1962 | Feinman | 75/26 |
| 3,356,488 | 12/1967 | Walsh | 75/34 |
| 3,761,244 | 9/1973 | Hoffert | 75/26 |
| 3,770,361 | 11/1973 | Heimberger | 425/445 |
| 3,885,023 | 5/1975 | Gray et al. | 423/439 |
| 3,928,021 | 12/1975 | Matsubara et al. | 75/35 |
| 4,045,214 | 8/1977 | Wetzel et al. | 75/60 |
| 4,053,301 | 10/1977 | Stephens, Jr. | 75/11 |
| 4,202,534 | 5/1980 | Davis, Jr. | 266/172 |
| 4,224,056 | 9/1980 | Tomizawa et al. | 75/11 |
| 4,360,378 | 11/1982 | Lindstrom | 75/34 |
| 4,398,945 | 8/1983 | Stephens, Jr. | 75/11 |
| 4,841,884 | 7/1989 | Engstrom et al. | 110/298 |
| 4,851,046 | 7/1989 | Low et al. | 106/35 |
| 5,073,194 | 12/1991 | Stephens et al. | 75/376 |
| 5,118,479 | 6/1992 | Stephens, Jr. et al. | 423/148 |
| 5,137,566 | 8/1992 | Stephens, Jr. et al. | 75/507 |

FOREIGN PATENT DOCUMENTS

WO89/09290 10/1989 WIPO.

OTHER PUBLICATIONS

Stephanopoulos, G., "Synthesis of Alternative Control Configurations for Multiple-Input, Multiple-Output Processes", Chemical Process Control. Prentice Hall, Inc. New Yersey, 1984 pp. 461–482.

Handa, A. et al., "Layer-By-Layer Analysis Of The Chemical State Of Iron In Carburized Steel Surfaces By Conversion Electron Mössbauer Spectrometry," pp. 1999–2002, 1981, *J. Mat. Sci.*, vol. 16, No. 7, Jul.

Oehlberg, R. J. et al., "FIOR Process For Direct Reduction Of Iron Ore," pp. 58–60, 1974, *Iron and Steel Engineer*, vol 51, No. 4, Apr.

Werther, J. et al., "MeBtechniken für Gas/Feststoff-Wirbelschichtreaktoren," pp. 605–612, 1990, *Chemie. Ingenieur. Technik*, vol. 62, No. 8, Aug. 2.

Amendment and Response filed during prosecution of Ser. No. 622,101, now U.S. Pat. No. 4,053,301 by Stephens, Inc. issued Oct. 11, 1977, date of response unknown.

*Primary Examiner*—David A. Redding
*Attorney, Agent, or Firm*—Sheridan, Ross & McIntosh

[57] ABSTRACT

A process for controlling the conversion of reactor feed to iron carbide is disclosed. The reactor feed is subjected to a process gas in a fluidized bed reactor (10), and the off-gas from this reaction is analyzed (56) to determine its composition and the temperature (64) and pressure (66). A stability phase diagram is generated based on the temperature. Different regions of the stability phase diagram are representative of different products being formed by the conversion of the reactor feed. Based on relative concentrations of the individual gases in the off-gas and the total pressure, a point is plotted on the stability phase diagram indicative of the favored reaction product. The process parameters can then be adjusted to insure that iron carbide can be produced from the reactor feed based on the stability phase diagram. In one embodiment, the rate of conversion of the reactor feed into iron carbide is controlled.

20 Claims, 3 Drawing Sheets

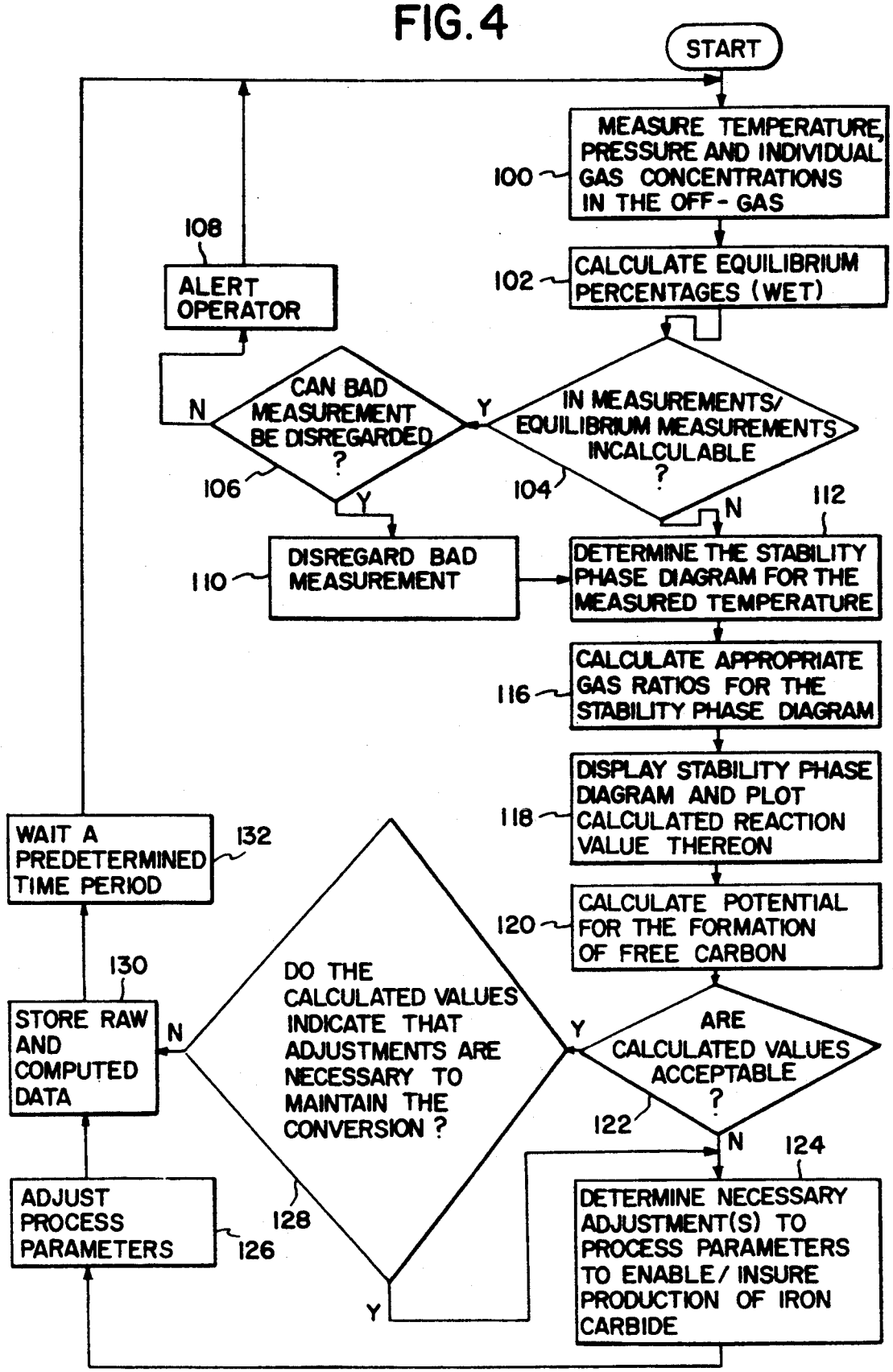

METHOD FOR CONTROLLING THE CONVERSION OF IRON-CONTAINING REACTOR FEED INTO IRON CARBIDE

REFERENCE TO RELATED APPLICATIONS

This application is a continuation-in-part of U.S. patent application Ser. No. 07/561,100 Hager et al., filed Aug. 1, 1990, now abandoned.

BACKGROUND OF THE INVENTION

1. Field of the Invention

The present invention relates to a process for converting iron-containing reactor feed into iron carbide, which is useful in the direct production of steel. More particularly, the present invention relates to controlling the conversion of reactor feed into iron carbide to assure that a suitable iron carbide product is produced.

2. Description of the Related Art

Typically, iron ore is converted to steel through a basic process that has been in use for many years. This process involves the conversion of iron ore to pig iron in a blast furnace using coke produced in a coke oven and the subsequent conversion of the pig iron to steel in an open hearth or basic oxygen furnace. However, this process has a number of drawbacks, some of which have been brought about by realities of life in the late twentieth century. For example, due to environmental standards, capital costs involved with the construction of a steel mill which meets pollution standards or the modification of existing plants to meet pollution standards would now be prohibitive. When the capital costs are factored into the price that must be charged for the steel produced by such a steel mill, the price of that steel would simply not be competitive on the world market. Additionally, the traditional steel-making process is energy intensive, and energy costs involved with making steel in the traditional manner have become excessive. With the availability and cost of energy in the near future being unpredictable, the traditional manner of manufacturing steel faces an uncertain future.

Accordingly, a demand has been created for relatively clean, energy efficient and less expensive methods for producing steel. In this regard, a great deal of effort has been directed to the elimination of the blast furnace and the coke oven in steel-making. Blast furnaces and coke ovens are inefficient, consuming large quantities of energy, and are responsible for a large portion of the pollution involved with steel-making. In this effort, some attention has been directed to the conversion of iron ore directly to iron carbide followed by the production of steel from the iron carbide, thereby eliminating the use of the blast furnace and the coke oven.

In this regard, U.S. Pat. No. Re. 32,247 by Stephens, Jr., dated Sep. 16, 1986, a reissue of U.S. Pat. No. 4,053,302 by Stephens, Jr. issued Oct. 11, 1977, discloses a process for the direct production of steel. Iron-containing reactor feed is converted to iron carbide, and steel is then produced directly from the iron carbide in a basic oxygen furnace or an electric arc furnace. In the converting step, the iron oxide in the reactor feed is reduced and carburized in a single operation using a mixture of hydrogen as a reducing agent and carbon-bearing substances as carburizing agents. The blast furnace step of traditional steel-making techniques is eliminated, as steel is then produced by introducing the iron carbide into a basic oxygen or electric arc furnace.

This method of directly producing steel represents a significant advance in the art. However, improvements in the method have proven desirable. It has been found that in the step of converting the reactor feed into iron carbide, even minor variations in the process parameters, which include pressure, temperature, and individual gas concentrations in the process gas, cause inferior results. That is to say, minor variations in any process parameter can cause free iron (Fe) or one of a variety of iron oxides, such as $Fe_2O_3$, $Fe_3O_4$ and $FeO$, to be included in the iron carbide product.

Therefore, there are significant problems associated with ensuring a suitable iron carbide product. Also, significant problems have been encountered in converting reactor feed into iron carbide at an acceptably high rate. Slow conversion of reactor feed to suitable iron carbide product can severely impair the commercial viability of a process.

As can be seen, a significant need exists for a process for producing a high quality iron carbide product at an acceptable conversion rate.

SUMMARY OF THE INVENTION

One aspect of the present invention is that it provides a method for controlling the conversion of iron-containing reactor feed into an iron carbide product from which steel can be readily produced. The reactor feed available for conversion to iron carbide ($Fe_3C$) is typically a mixture of magnetite ($Fe_3O_4$), hematite ($Fe_2O_3$) and other materials, rather than consisting entirely of one material. The reactor feed may also include some gangue and water. As used herein, the term reactor feed refers to any material useful in the practice of the present invention, for example, iron ore and iron ore concentrates.

Another aspect is that the present invention provides a method for controlling the conversion of reactor feed to iron carbide in a manner in which changes can be effected to correct deviations in process parameters on a real time basis.

Another aspect of the present invention is providing a method for controlling the rate of conversion of reactor feed to iron carbide.

In accordance with the present invention, a method is provided for maintaining process parameters within a predetermined range for the conversion of iron-containing reactor feed into a product chiefly comprising iron carbide in a fluidized bed reactor. The process includes the steps of monitoring gas concentrations for at least two individual gases in a reaction gas in a region substantially adjacent to the fluidized bed reactor, measuring pressure and temperature in the region, determining gas concentrations for remaining individual gases in the reaction gas (e.g., by thermodynamic calculation and/or by direct measurement), determining whether the process parameters are suitable for the production of iron carbide, and adjusting individual gas concentrations as necessary to permit the conversion of reactor feed to iron carbide. The process parameters to be maintained include the temperature, the pressure and the individual gas concentrations.

Preferably, the region in which pressure and gas composition measurements are taken is directly above the fluidized bed and the reaction gas is the equilibrium off-gas from the conversion of reactor feed into iron carbide. Additionally, the gas concentrations are preferably monitored using two different measurement techniques, with the monitored gas concentrations being compared to determine if an error in measurement has been made.

Also in accordance with the present invention, a method is provided for generating a stability phase diagram indicative of the conversion of reactor feed. The process includes the steps of measuring individual gas concentrations in a region substantially adjacent to a fluidized bed reactor in which the conversion is taking place, measuring temperature and pressure in this region, determining concentrations of remaining gases (e.g., thermodynamically and/or by measurement) and generating a stability phase diagram indicative of whether the measured and/or calculated gas concentrations are suitable for the production of iron carbide from the reactor feed at the measured temperature and pressure.

Preferably, the measured individual gases include at least two gases from the group consisting of carbon monoxide (CO), carbon dioxide ($CO_2$), methane ($CH_4$), hydrogen ($H_2$) and water ($H_2O$). Further, the gas concentrations are preferably measured using two different measurement techniques. For the CO and the $CO_2$, the preferred techniques are infrared light absorption, mass spectroscopy and gas chromatography. For $H_2$, the preferred techniques are thermal conductivity, gas chromatography and mass spectroscopy. Preferably, the steps of the method are repeated after a predetermined period of time for updating purposes. Additionally, in one embodiment the individual gases are preferably measured on a dry basis, the reaction gas being dried prior to the measurement(s) being made. The volume of any remaining gases is then determined on a dry basis thermodynamically, and then the gas composition is calculated on a wet basis for the measured temperature and pressure.

The present invention is further embodied by a method for controlling the conversion of iron-containing reactor feed to iron carbide in a fluidized bed reactor which comprises the steps of monitoring the composition of reaction gas in a zone substantially adjacent to the fluidized bed reactor, monitoring the pressure and temperature in the zone, determining whether the process parameters are suitable for the production of iron carbide from the reactor feed, adjusting the process parameters to permit production of iron carbide, and repeating the steps after a predetermined period of time.

In one embodiment, the present invention involves controlling the rate of conversion of iron-containing reactor feed to iron carbide by maintaining temperature and gas concentrations such that a high quality iron carbide product is produced at an enhanced rate of production. In one embodiment, the volume fraction of reducing gas in the reactor gas mixture is maintained near a maximum value. In another embodiment, the temperature is maintained at from about 400° C. to about 700° C., and preferably between 525° C. and 600° C., and the pressure is increased to a point where further increases in pressure would result in a lowering of the volume fraction, or volume percentage, of hydrogen in the reaction gas composition. In another embodiment, the pressure is maintained at from about 1 atmosphere to about 6 atmospheres, absolute, preferably from about 2 atmospheres to about 5 atmospheres, more preferably from about 3 atmospheres to about 5 atmospheres and most preferably from about 3.5 atmospheres to about 4.5 atmospheres. In another embodiment, the iron-containing particles in the feed material are smaller than about ⅛" (3.8 mm) in size.

In one embodiment of the invention, greater than about 90%, and preferably greater than about 95%, of the iron in the feed material is converted to iron carbide with less than about 35 hours retention time in the reactor, preferably with less than about 20 hours retention time, and more preferably less than about 17 hours retention time. In another embodiment hydrogen comprises about one-third of the reactive gases, on a volume basis. In another embodiment, each mole of iron in the feed material is treated with greater than about 1.1 moles reaction gas per hour, and preferably greater than about 2.0 moles reaction gas per hour.

BRIEF DESCRIPTION OF THE DRAWINGS

FIG. 4 illustrates a flow chart of the control process according to an embodiment of the present invention.

DETAILED DESCRIPTION OF THE INVENTION

The present inventors have developed an improved technique for converting iron-containing reactor feed to iron carbide, and more particularly, to $Fe_3C$, which the inventors have found is the predominant form of iron carbide which is produced. In this technique, reactor feed, which typically comprises a mixture of iron oxides such as magnetite ($Fe_3O_4$) and hematite ($Fe_2O_3$), along with other materials such as gangue and water, is converted to iron carbide in a fluidized bed reactor.

Prior to being introduced into the reactor, the reactor feed can be preheated in an oxidizing atmosphere. During the preheating, a portion of any magnetite present can be converted to hematite, sulfur in the ore can be stabilized and/or eliminated, and free moisture can be reduced or eliminated. It is believed that the oxidation of the magnetite to hematite provides for more efficient conversion of reactor feed into iron carbide. The elimination of sulfur is believed to increase the yield of iron carbide in the final product. Further, by reducing the amount of water entering the fluidized bed reactor, the conversion of iron oxide to iron carbide is improved. This technique is described in more detail in commonly assigned U.S. patent application No. 07/561,189 by Stephens, Jr, et al. filed Aug. 1, 1990, now U.S. Pat. No. 5,137,566 issued Aug. 11, 1992, entitled "Process For Preheating Iron-Containing Reactor Feed Prior To Being Treated In A Fluidized Bed Reactor" which is incorporated herein by reference in its entirety.

Figure 1:
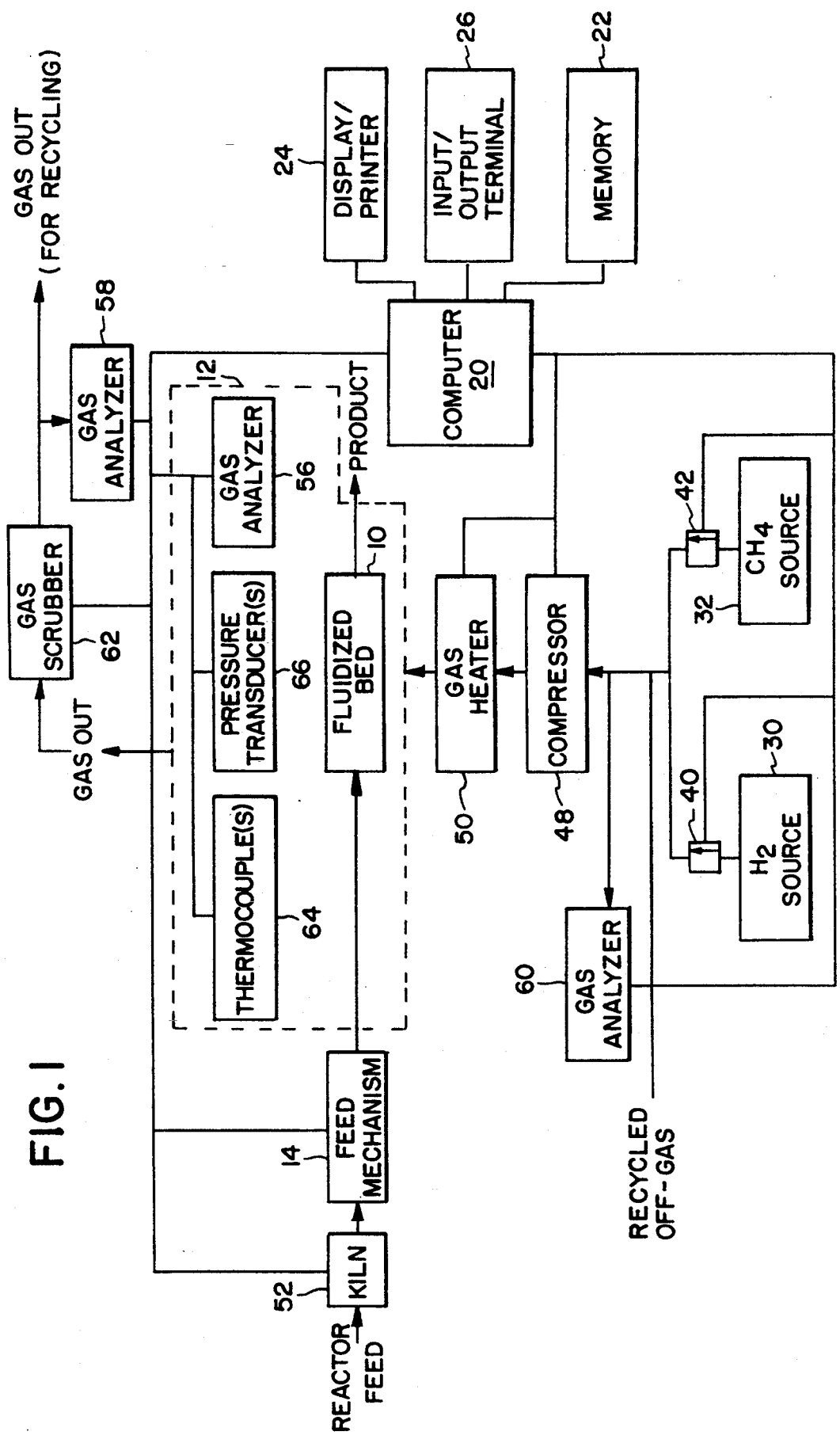
FIG. 1 is a schematic diagram of a control system according to an embodiment of the present invention.

A system through which control of the conversion of reactor feed to iron carbide is performed is illustrated in FIG. 1. A fluidized bed 10 is schematically illustrated in a fluidized bed reactor 12. The fluidized bed reactor 12 is described in more detail in commonly assigned U.S. patent application No. 07/561,076 by Stephens, Jr. et al., filed Aug. 1, 1990, now U.S. Pat. No. 5,118,479 issued Jun. 2, 1992, entitled "Fluidized Bed Reactor And Process For Using Same," which is incorporated herein by reference in its entirety. Preferably the fluidized bed 10 includes baffles to create a plug flow condition. The baffles help regulate the residence time of the reactor feed in the fluidized bed 10, thus reducing problems caused by short-circuiting of unreacted solids to the product discharge and utilizing the full area of the bed 10. This permits efficient use of incoming process gas in contacting reactor feed as it flows through the fluidized bed 10 for converting the reactor feed to iron carbide.

The input or process gas used to convert the reactor feed to iron carbide includes reducing and carburizing agents. Hydrogen gas ($H_2$) is preferably used as the reducing gas, although carbon monoxide or hydrocarbon gases or mixtures of hydrogen with carbon monoxide and hydrocarbon gases may be used. Hydrogen gas is preferred as the reducing gas because the oxidation product of hydrogen, water, may be easily removed from the reaction or off-gas, thereby permitting easier recycling of the off-gas than with the other possible reducing gases. Methane is preferred for the carburizing agent, although carbon monoxide, carbon dioxide, hydrocarbon gases and solid carbon may be used. Additionally, the source of the methane gas may be other hydrocarbon gases or a combination of gases that would crack or otherwise combine to form methane under the conditions present in the reactor chamber 12. In theory, a wide range of carbonaceous materials may be used to supply the carbon necessary for the formation of iron carbide.

Regardless of the input gas, the equilibrium off-gas system (or reaction gas) comprises five gases. These include water ($H_2O$), carbon monoxide (CO), carbon dioxide ($CO_2$), hydrogen ($H_2$) and methane ($CH_4$). Additionally, there may be some nitrogen ($N_2$) present in the system. Whatever process or input gases are actually used, by reacting these gases in rather precise quantities with the reactor feed at certain temperatures and pressures, the reactor feed is converted to $Fe_3C$, the preferred type of iron carbide.

Figure 2:
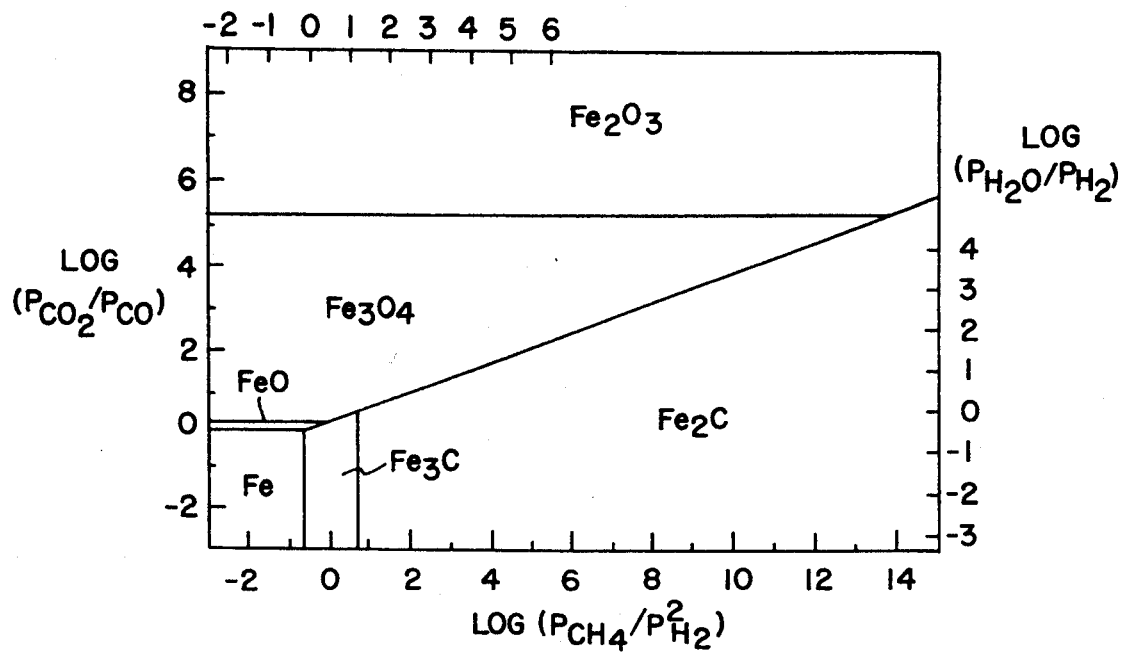
FIG. 2 is a Fe-O-H-C stability phase diagram.

Without process control, equilibrium constraints cause the formation of products other than iron carbide due to even minor deviations in process parameters. Additionally, at higher conversion temperatures, residual oxygen in the product in the form of wustite can limit the efficiency of the conversion of the product to steel. FIG. 2 is a stability phase diagram for the conversion of iron oxide at a temperature of 677° C., which is independent of pressure. The system pressure does, however, affect the portion of the stability phase diagram in which the system can operate. This diagram illustrates the wide range of products that may result from the conversion process.

The present inventors have developed a unique control regimen for the conversion process described above. The present inventors have found that, in accordance with the equilibrium constraints for the conversion of iron-containing reactor feed into iron carbide, the off-gas from the reaction will include hydrogen ($H_2$), carbon monoxide (CO), carbon dioxide ($CO_2$), methane ($CH_4$) and water vapor ($H_2O$) in determinable concentrations or concentration ranges, dependent upon the temperature and pressure. Typically, the off-gas will also include nitrogen gas ($N_2$) or other inert gas, which is a diluent and does not react with the reactor feed. By monitoring characteristics of the off-gas and making appropriate changes to the make-up of the process gas, temperature, pressure and other process parameters in response to the monitored characteristics, conditions can be maintained in the fluidized bed reactor 12 that will maximize the conversion of reactor feed to iron carbide.

In order to best regulate the conversion process, a process gas including $CH_4$, $H_2$, CO, $CO_2$, $H_2O$ and $N_2$ at a controlled temperature and pressure is supplied through a windbox (not illustrated) to the fluidized bed 10. The temperature and pressure in the bed 10 are two of the factors which determine the composition of the reaction product. The independent equilibria equations for the process gas in the reaction chamber can be described by:

$$CO + H_2O \sim CO_2 + H_2; \text{ and}$$

$$CH_4 + H_2O \sim CO + 3H_2.$$

Accordingly, based on these reactions, the off-gas will comprise $CH_4$, $H_2$, CO, $CO_2$ and $H_2O$ (in addition to inert diluents), the equilibrium gases having determinable relationships to each other. The volume percent of CO in the process gas is preferably up to about 20%, and more preferably from about 1% to about 10%; the volume percent of $CO_2$ up to about 20%, and more preferably from about 1% to about 8%; the volume percentage of $CH_4$ up to about 80%, and more preferably from about 35% to about 50%; the volume percent of $H_2$ up to about 80%, and more preferably from about 35% to about 50%; the volume percent of $N_2$ from 0% to about 15%, and more preferably from about 1% to about 10%; and the volume percent of $H_2O$ up to about 5%, and more preferably from about 1% to about 2%. The exact percentages will be different for each combination of temperature and mole ratios of hydrogen to oxygen and of carbon to oxygen.

In one embodiment, the reaction temperature is preferably maintained between about 400° C. and about 700° C., most preferably between about 500° C. and about 650° C., even more preferably between about 525° C. and about 610° C. and most preferably from about 570° to about 600° C. In another embodiment, the reaction pressure is be maintained at from about 1 atmosphere to about 6 atmospheres, preferably from about 2 atmospheres to about 5 atmospheres, more preferably from about 3 atmospheres to about 5 atmospheres, and even more preferably from about 3.5 atmospheres to about 4.5 atmospheres. In one embodiment, the pressure is maintained at about 4 atmospheres. All pressures referred to herein are absolute.

Stability phase diagrams for each temperature at which the conversion occurs are different. That is to say, while a process gas having a given composition of individual gases can provide equilibrium conditions that favor the formation of $Fe_3C$ at one temperature, the identical process gas composition can favor the formation of free iron or an iron oxide at a different temperature.

To effect control of the conversion, a computer 20 monitors temperature, pressure and gas composition in a region substantially adjacent to the fluidized bed 10 where the gas from the reaction in the fluidized bed 10 flows following the reaction. Typically, this region is above the bed 10. A memory 22 associated with the computer 20 stores data with which the computer 20 can develop a stability phase diagram for the instant temperature and pressure using the following techniques. The stability diagram for the Fe-O-H-C system relates to the stable condensed phases as a function of temperature and the partial pressures of $CH_4$, $H_2$, CO and $CO_2$. The relative chemical potential of oxygen in the system is defined through the use of the logarithm of the partial pressure ratio $CO_2$ to CO, i.e., log $[P(CO_2)/P(CO)]$. The relative chemical potential of carbon in the system is defined through the use of logarithm of the ratio of the partial pressure of $CH_4$ to the square of the partial pressure of $H_2$, i.e., log $[P(CH_4)/[P(H_2)]^2]$. The phase boundaries in the diagram are constructed by first writing a balanced chemical reaction between the condensed phases and the gaseous species used in defining the oxygen and carbon potentials ($CO_2$, CO, $CH_4$ and $H_2$). For the $Fe_3O_4/Fe_3C$ boundary, the reaction is:

$$Fe_3O_4 + CH_4 + 4CO \sim Fe_3C + 2H_2 + 4CO_2.$$

The equilibrium constant for the reaction can then be written in logarithmic form and serves to define the equation describing the phase boundary. For the above reaction, the relationship is $$\log K = 4\log \frac{PCO_2}{PCO} - \log \frac{PCH_4}{(PH_2)^2},$$

which can be rearranged to give the equation defining the boundary $$\log \frac{PCO_2}{PCO} = \frac{1}{4} \log \frac{PCH_4}{(PH_2)^2} + \frac{1}{4} \log K.$$

The values of log K are determined from the expression $$\Delta G°(RXN) = -RT\ln K,$$

where $\Delta G°$ (RXN) is the change in the Gibbs Free Energy for the reaction. Values of $\Delta G°$ (RXN) are calculated from tabulated Gibbs Free Energy of formation data given for the different species involved in the reactions defining the phase boundaries.

The Fe-O-H-C stability diagrams are particularly useful in determining the stable condensed iron-containing phases under measured or proposed conditions of gas compositions, temperature and pressure. The temperature must first be specified since the $\Delta G°$ (RXN) values are a function of temperature and thus the diagram constructed for the appropriate temperature. Alternatively, rather than in terms of the ratios of the partial pressures of $CO_2$ to CO and of $CH_4$ to $H_2$, the boundaries of the stability phase diagram can be expressed in terms of the partial pressures of CO to $CO_2$ and of $H_2O$ to $H_2$, i.e., log $[(P(CO))^2/P(CO_2)]$ and log $[P(H_2O)/P(H_2)]$.

Figure 3:
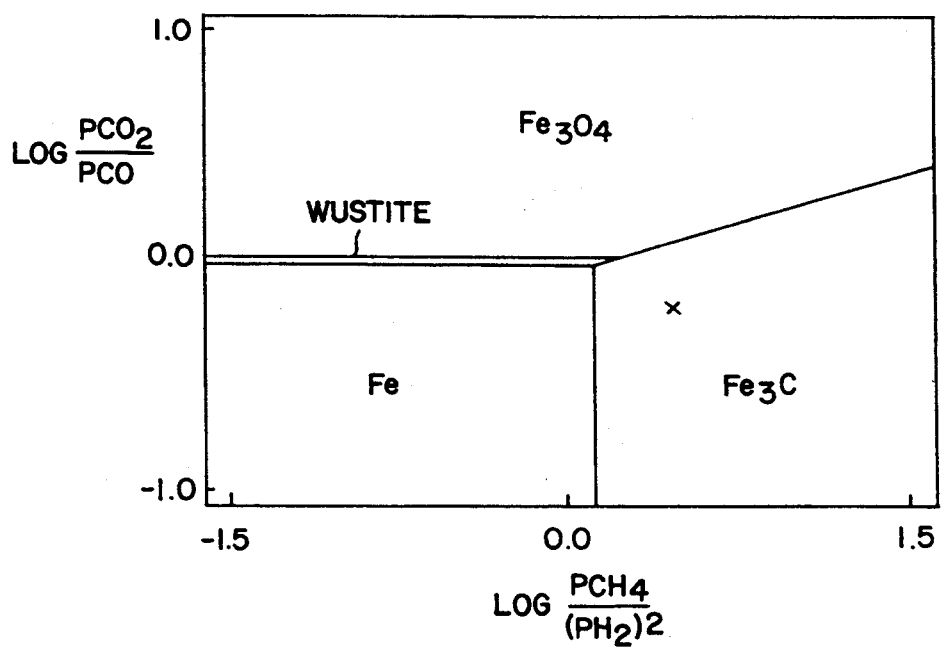
FIG. 3 is a Fe-O-H-C stability phase diagram at a given temperature and pressure with a point plotted for a given gas composition.

FIG. 3 illustrates a stability phase diagram developed from this procedure for a temperature of 580.0° C. and a gas mixture at a pressure of 26.5 psia.

As discussed above, the composition of the conversion product produced in the fluidized bed 10 is dependent on the relationships between the concentrations of the individual gases in the reaction gas at the instant temperature and pressure. Correspondingly, the reaction gas from the conversion must have certain relationships between individual gas components for a conversion to iron carbide to have occurred. The inventors have used this fact to provide for control of the conversion process.

As discussed above, a stability phase diagram for each temperature is generated with each axis of the diagram representing a different relationship between the individual gases. Each point on a stability phase diagram represents a unique gas composition in the five-species gas system at a given temperature and total pressure.

Only certain relationships between the gases will have resulted from iron carbide being produced. The inventors have found that it can be determined whether iron carbide production is possible based on these relationships. Based on the equilibrium constraints, these include the relationships between the $CO_2$ concentration with respect to the CO concentration or the $H_2O$ concentration with respect to the $H_2$ concentration and the CO concentration with respect to the $CO_2$ concentration or the $CH_4$ concentration with respect to the $H_2$ concentration. The concentrations used are the equilibrated wet basis gas concentrations.

Generally speaking, the relationships between the gases necessary to produce iron carbide can be described in broad terms. For example, for gas concentration ratios, it can be said that the ratio of $CO_2$ to CO should be from about 1:1 to about 1:10, the ratio of $CH_4$ to $H_2$ should be from about 1:1 to about 5:1, and the ratio of $H_2$ to $H_2O$ should be from about 4:1 to about 40:1. However, whether a particular reaction gas will have resulted from iron carbide ($Fe_3C$) being produced must be computed for each combination of pressure, temperature and reaction gas composition, and can be plotted on a stability phase diagram for a given temperature and pressure. The partial pressure of the individual gases can be calculated from the gas composition and total pressure using the relationship $$P_i = \left(\frac{\% i}{100}\right) P_T$$

where $P_i$ is the partial pressure of gaseous species i, (% i) is the volume percent of i, and $P_T$ is the total pressure in atmospheres. The phase field identified by the calculated x and y coordinates is the thermodynamically stable phase. Partial pressures (P) used in the construction of the diagrams shown are all in atmosphere units. It is possible to translate the log coordinates from a stability phase diagram into gas compositions, and vice versa, based on the equilibrium constraints represented by the independent equilibria described above. By this translation, it is possible to develop data permitting the calculation of a gas composition corresponding to the triple point where Fe, $Fe_3O_4$, and $Fe_3C$ are in equilibrium, in terms of conversion to free iron (Fe), $Fe_3O_4$ and $Fe_3C$, as a function of the gas compositions, temperature and pressure. Using this technique it is also possible to determine and show graphically on the stability phase diagram for a particular temperature and pressure whether or not iron carbide will be the product with a given reaction gas composition. For example, Table 1 below gives the measured composition (on a dry basis) of the individual gases in a reaction gas at a measured temperature and pressure.

TABLE I

| Measurement Taken on Dry Basis | |
|---|---|
| GAS | PERCENTAGE (BY VOLUME) |
| CO | 8.00 |
| $CO_2$ | 5.00 |
| $CH_4$ | 50.00 |
| $H_2$ | 33.00 |
| $N_2$ | 4.00 |

The $H_2O$ content of the wet off-gas is then measured or calculated based on the expected amount of $H_2O$ in accordance with the equilibrium constraints. The sampled gas composition on a wet basis is provided in Table II.

TABLE II

Calculated Gas Composition (Wet Basis)

| GAS | PERCENTAGE (BY VOLUME) |
|---|---|
| CO | 7.52 |
| $CO_2$ | 4.70 |
| $CH_4$ | 47.00 |
| $H_2$ | 31.02 |
| $N_2$ | 3.76 |
| $H_2O$ | 6.00 |

The temperature and pressure in the reactor 12 are stored in memory 22. In this example, the reactor temperature was 580.0° C. and the reactor pressure was 26.5 psia (1.8 atm, 182 kPa). Based on these data, the computer 20 calculates the equilibrated wet gas composition at the reactor temperature and pressure. This composition is provided in Table III.

TABLE III

Equilibrated Wet Gas Composition

| GAS | PERCENTAGE (BY VOLUME) |
|---|---|
| CO | 7.56 |
| $CO_2$ | 4.60 |
| $CH_4$ | 47.16 |
| $H_2$ | 30.71 |
| $N_2$ | 3.77 |
| $H_2O$ | 6.20 |

Based on the equilibrated wet gas composition, the appropriate calculations are made. For example, the y coordinate for this measurement and diagram is $$\log_{10}\left(\frac{PCO_2}{PCO}\right) = \log_{10}\left(\frac{(0.0460)(1.803)}{[(0.0756)(1.803)]}\right) = -0.2158,$$

and the x coordinate is $$\log_{10}\left(\frac{PCH_4}{(PH_2)^2}\right) = \log_{10}\left(\frac{(0.4716)(1.803)}{[(0.3071)(1.803)]^2}\right) = 0.4430.$$

The computer then plots this point on the stability phase diagram (illustrated at "X" of FIG. 3), indicating the relationships between the gases (on a wet basis). Under the measured conditions listed in Table I, the point falls in the $Fe_3C$ region, indicating that iron carbide ($Fe_3C$) should be formed from the reactor feed under the measured parameters (i.e., temperature, pressure, equilibrium reaction gas composition).

The computer 20 is preferably programmed to independently ascertain whether or not the current process parameters will form iron carbide based on the data which is used to create the stability phase diagram for the specific temperature and the off-gas data used to plot the point on the diagram. If the parameters are not favorable for the conversion to $Fe_3C$, the computer 20 will then determine and implement the necessary changes to the process so that the relationships between the individual gases, temperature and pressure are such that the feed will convert to iron carbide.

Preferably, the stability phase diagram is displayed to an operator at display 24, which may comprise a printer or a CRT. Preferably the computer 20 automatically implements adjustments to the process parameters to cause iron carbide to be produced or to compensate for any trend which may result in iron carbide not being produced at a future time. Optionally, the operator may be directly responsible for adjusting the parameters via the computer 20 through a computer terminal 26 after viewing the stability phase diagram from the display 24. The function of the operator can be to input all changes to the process parameters based on the data generated by the computer 20, to assist the computer 20 should the programming not foresee all situations or if the computer can adjust only certain parameters, or to override the computer 20 and manually input new process parameters depending upon the requirements of any given situation or the limitations of the computer 20.

As discussed above, the process gas preferably comprises a combination of hydrogen ($H_2$), and methane ($CH_4$). These gases may be provided by respective gas sources 30,32, which may be containers storing the gas. Alternatively, and preferably, the process gas also includes CO, $CO_2$ and/or $H_2O$ and the sources 30,32 provide a make-up gas used to supplement recycled off-gas to obtain a process gas having desired concentrations of the individual gases. As will be appreciated, other gases or compounds can be added to provide the requisite hydrogen, carbon and oxygen sources. Whatever the source of these materials, the resulting equilibrium reaction gas will include $H_2$, CO, $CO_2$, $CH_4$ and $H_2O$. In any case, the amount of each gas added to the overall process gas is controlled by respective valves 40,42 which are controlled by the computer 20. When new gas is to be added to recycled off-gas, measurements from gas analyzers 56,58 can be used to determine what the composition of the recycled off-gas should be, and appropriate amounts of the individual gases can be added as necessary to obtain a process gas having a composition needed to react with the reactor feed and result in the appropriate off-gas. In this regard, the gas analyzer 60 can also be used to monitor the composition of the recycled off-gas and/or the flow rates from the gas sources 30,32.

Because of the existence of $N_2$ and/or other inert gases in the system, the recycling system must typically include a bleed to prevent the build-up of such gases in the system. However, an additional advantage of the present invention is that inexpensive gas sources that include such inert gases may be employed without significantly affecting the conversion.

The pressure in the reactor 12 can be controlled by the amount of $H_2$ added to the process gas. While other techniques are possible, this technique is favored, One reason is that since $H_2$ combines with oxygen from iron oxide, there is always a need for some $H_2$ in the reactor 12, although an increase or decrease in $H_2$ may require adjusting other parameters.

The process gas is supplied to a gas compressor 48 and then heated in a gas heater 50 to a desired temperature for the conversion. The gas heater 50 is also controlled by the computer 20, as is a secondary heat source 52, in order to control the temperature of conversion in the reactor 10. The secondary heat source 52 is preferably a kiln or other such device that is used to preheat the reactor feed. By changing the temperature to which the reactor feed is heated in the kiln 52, the temperature at which the feed is fed into the fluidized bed reactor 12, and thus the reaction temperature, can be controlled (in combination with the control of the gas heater 50).

The control process will now be described with additional reference to the flow chart of FIG. 4.

As discussed above, the reactor feed is preferably preheated and oxidized in a kiln 52. The oxidized feed is then introduced to the fluidized bed reactor 12 by a feed mechanism 14 and flows therethrough, being converted to iron carbide when an appropriate combination of gases at an appropriate temperature and pressure is bubbled through the feed in the reactor bed 10. Measurements are then taken of the off-gas, that is, the reaction gas which has fluidized the feed in the fluidized bed 12. As discussed above, water vapor is typically removed from the off-gas prior to the composition of the off-gas being measured. The temperature and pressure are measured in a region substantially adjacent to the bed 10 (step 100 in FIG. 4). Preferably, at least two measurements for each species in the off-gas are taken using different measurement techniques and at different stages of the processing of the off-gas, as discussed above and discussed in more detail below. When the temperature and pressure are known and when the concentrations of at least two of the gases are known, the concentration of each gas in the off-gas can be determined thermodynamically. By knowledge of the individual gas concentrations at a given temperature and pressure, it can be determined whether or not the production of iron carbide is possible based on the equilibrium constraints. Thus, a stability phase diagram indicating anticipated conversion results can be generated by knowing as few as two of the five equilibrium gas components, along with the temperature and pressure. For example, if either the carbon monoxide and carbon dioxide or the hydrogen, water and methane concentrations are determined, then the concentrations of the remaining gas species can be calculated thermodynamically.

However, a small error in the measurement of one of the two gas species can result in a larger error in the calculated species. Accordingly, the preferred method is to measure each of the individual gases in the off-gas on a dry basis (step 100) and then convert each measurement set to equilibrium wet measurements (step 102). Among other advantages, this permits the computer 20 to evaluate the measurements for inaccuracies. To help further insure against the possibility of inaccuracies, it is preferred that at least two measurement techniques be utilized simultaneously to monitor each of the individual gases in the off-gas (dry basis), with the computer 20 being programmed to respond to deviations in individual gas concentrations between the two monitoring techniques. If a deviation between measurements is found or if an equilibrium cannot be calculated (indicative of a measurement error) (step 104), the computer 20 can alert the operator (step 108), take new measurements (step 100), and/or attempt to determine which of the measurements is incorrect by the thermodynamic calculations (step 106) and then discard the incorrect measurement (step 110) and proceed with the control process.

As shown in FIG. 1, a gas analyzer 56 measures off-gas in the region just above the fluidized bed reactor 10. Gas chromatography is a preferred method for monitoring individual gas concentrations from the off-gas from this region. For example, a "Vista" model gas chromatograph available from Combustion Engineering can be employed for this purpose. This method is very effective and accurate in measuring CO, $CO_2$, $CH_4$, $H_2$, $N_2$, and other hydrocarbon concentrations. Preferably, an off-gas sample is removed from the region above the reactor 10 and the water vapor removed prior to gas chromatography being performed on the sample, measuring the gas on a dry basis. The data is then supplied to the computer 20. At the computer 20, the measurements are then adjusted by the estimated, or measured, water vapor concentration above the reactor 10. Finally, the measured temperature and pressure are taken into account to obtain the equilibrated wet-basis composition of the off-gas.

Another measurement technique that may be used in combination with gas chromatography is infrared light absorption. Carbon monoxide and carbon dioxide are easily and accurately measured continuously using infrared light absorption technology. The infrared light absorption technique provides continuous measurement and rapid response information to the operator and the computer 20. This technique may also be used for monitoring methane. However, the methane measurement is subject to interference from other gaseous hydrocarbons. Further, water vapor in a gas sample is known to interfere with measurements taken using the infrared light absorption technique. Accordingly, water vapor is reduced or removed from the off-gas prior to the off-gas being measured using this technique. Using this technique, gas analyzer 58 takes samples of the off-gas after water vapor is removed in a scrubber 62. The analyzer 58 may include an infrared absorption dual gas analyzer, such as a Model IR-702 from Infrared Industries, Inc., for monitoring CO and $CO_2$ concentrations. The gas analyzer 58 may also include a single gas infrared absorption analyzer for monitoring the methane concentrations. A Model IR-703 single gas analyzer from Infrared Industries, Inc. may be employed for this purpose.

Mass spectroscopy is another technique which can be utilized for monitoring individual concentrations of gas in the off-gas. Mass spectroscopy is especially useful for measuring concentrations of hydrogen, water, methane and any higher hydrocarbons. The analyzer 58 may include such a device, which may be, for example, a Questor model mass spectrometer manufactured by Extriel.

Additionally, hydrogen can be continuously measured by thermal conductivity with reasonable accuracy. One advantage of measuring hydrogen by thermal conductivity is that this method is continuous and provides rapid response information to the operator and the computer. The gas analyzer 58 may also or alternatively include a thermal conductivity process analyzer, which can be a model Caldos-5 available from Applied Automation/Hartman & Braun, Inc.

A third gas analyzer 60 may additionally be employed by the system. The gas analyzer 60 would preferably be stationed to take samples from the input process gas, which preferably comprises a combination of the recycled off-gas and make-up gas from the gas sources 30,32. The gas analyzer 60 may be of the type(s) described above.

Temperature is measured in the region adjacent to the fluidized bed 10, using at least one thermocouple 64. Suitable thermocouples include Chromel-Alumel Type K thermocouples. Pressure is measured in the region with at least one pressure transducer 66. Appropriate pressure transducers can be obtained from the Yokogawa Corporation of Japan.

Data from the gas analyzers 56, 58, 60, the thermocouple(s) 64 and the pressure transducer(s) 66 are provided to the computer 20. The computer 20 can be an IBM AT compatible personal computer. Analog signals from the gas analyzers, thermocouple(s) and pressure transducer(s) are converted to digital signals and fed to the computer 20 via an interface card. As mentioned above, the gas composition is measured on a dry basis. Accordingly, the computer 20 must compute the gas composition on a wet basis, and account for any shift which may have occurred due to changes in temperature and pressure, by calculating the equilibrated off-gas composition based on the measured reactor pressure and temperature (step 102 in FIG. 4).

After recalculating the gas composition on a wet basis at the reactor temperature, the computer 20 then computes the corresponding stability phase diagram for the temperature measured by the thermocouple(s) 64 (step 112 in FIG. 4). Referring to FIG. 4, the program then uses the computed theoretical gas composition at the measured pressure to calculate the appropriate relationships between the gases for which the diagram is designed to display (step 116). The stability diagram of FIG. 3 is designed for the log (partial pressure of $CO_2$/partial pressure of CO) and the log [(partial pressure of $CH_4$)/(partial pressure of $H_2)^2$], which are the x- and y-axes of the stability phase diagram. As discussed above, other relationships between the gases may be used. The stability phase diagram including the point calculated in step 116 indicating the above relationships between the individual gases in the off-gas is then displayed on the display 24 (step 118) to graphically illustrate whether or not the process conditions are suitable for the production of iron carbide. An example of such a display is shown in FIG. 3, with the equilibrated gas composition resulting in plotted point "X."

Based on the received and processed data, the computer 20 can also compute the potential for the formation of free carbon in the conversion process (step 120). When a carbon activity is too high, solid free carbon may form. Solid free carbon does not readily reconvert to gaseous form, and will clog heat exchangers or other components of the conversion system. If free carbon is permitted to form as part of the product, a major fire hazard exists, since the free carbon is quite flammable. It has been found that if the carbon activity is greater than a quantity in a range of from about 4 to about 6, steps must be taken to lower the ratio to prevent the formation of free carbon. Preferably, the carbon activity is maintained in a range of about one to about four, and more preferably from about two to about three.

At this time, if it is determined that the values are not acceptable (step 122), either the computer 20 or the operator or both determine what adjustment(s) to the process parameters is necessary (step 124), and make the appropriate adjustment(s) (step 126).

If the calculated values are found to be acceptable, a determination is then made as to whether any trend is indicated that would lead to iron carbide not being produced (step 128). If some trend is indicated, based on a comparison with prior measurement(s), necessary adjustments to the conversion process are determined (step 124) and implemented (step 126).

For example, if it is determined that free iron (Fe) will be produced by the present process parameters, one solution for changing the process parameters to a desired combination would be to increase the amount of carbonaceous materials in the process gas. This can be accomplished by increasing the amount of methane provided by the methane source 32 into the process gas. Alternatively, a change in the temperature and/or pressure will affect the location of phase boundaries on the x-axis of the stability phase diagram. By an appropriate changer the same gas composition can result in the formation of iron carbide. Such changes can be implemented by increasing the temperature of the kiln 52 and/or the temperature to which the process gas is heated in the gas heater 50. The pressure can be increased or decreased by adjusting the amount of gases provided by the gas sources 30,32.

If it is determined that $Fe_3O_4$ is being produced, but the value for the methane to hydrogen ratio (the x-axis) is acceptable, then it is likely that the oxygen potential in the system is too high. Oxygen is provided to the reactor 12 in the form of iron oxide. Accordingly, the amount of oxygen can be reduced by adjusting the feed mechanism 14 to decrease the feed rate to the reactor 12. Alternatively, additional oxygen may be removed from the off-gas in the recycling steps. This can be accomplished by lowering the temperature of the off-gas leaving the scrubber 62 by lowering the temperature of cooling water or increasing the flow of the cooling water. Concurrently, the flow rate of the off-gas can be increased to cause the total volume of gas being scrubbed to increase thereby causing more water to be removed by the scrubber 62.

Should the stability phase diagram indicate that neither the calculated $CO_2$ to CO ratio nor the $CH_4$ to $H_2$ ratio are appropriate for the formation of iron carbide (the point plotted on the stability diagram is above the iron carbide area and to the left of the iron carbide area), then a combination of the adjustments discussed above for the previous two situations would be in order.

Should the ratio for the formation of free carbon be too high, the point plotted on the stability phase diagram will typically be found in the right portion of the area indicating that $Fe_3C$ is being formed. A solution is to increase the amount of $H_2$ in the process gas, thereby lowering the ratio and moving the point to the left portion of the $Fe_3C$ region.

The above list of possible adjustments is by no means exhaustive, and other solutions are possible to correct or maintain the process depending on the specific parameters on which the process is operating and which are controllable.

Similarly, measurements supplied to the computer 20 may indicate that iron carbide is being produced. However, upon comparing measurement data with stored measurement data from earlier measurements, trends may be detected that, if unchanged, would result in iron carbide not being produced in the future. In response to such a finding, the computer 20 or an operator can adjust the parameters as discussed above depending upon the trend.

After the necessary adjustments are made or if no adjustments are deemed necessary, the raw and computed data are stored in memory 22 for future use (step 130). This enables historical trend lines to be developed. This will assist in further refining of the control process as trends can be discovered far in advance of any detrimental event.

Preferably, the entire sequence is repeated after a very short period of time. A delay of a predetermined period of time can be built into the system (step 132), or new measurements can be taken and new data made available as soon as possible, which, depending on the measurement equipment and the power of the computer 20, can be as soon as every few seconds.

In one embodiment of the present invention, the rate of production of iron carbide is controlled, and preferably maximized, through adjustment of the concentration of reducing gas in the reactor. Typically, the reducing gas will be hydrogen. The inventors have, surprisingly, discovered that certain higher pressures than previously used for production of iron carbide can improve iron carbide production efficiency, especially when combined with certain preferred temperature ranges.

It has been discovered that the rate of conversion of reactor feed to iron carbide is generally higher at higher treating rates with reducing gas. Therefore, higher concentrations of reducing gas in the reaction gas mixture are generally preferred. In one embodiment, wherein the reducing gas is hydrogen, it has been found generally desirable to maximize the concentration of hydrogen, within practical limits, in the reaction gases that contact the reactor feed for conversion of reactor feed to iron carbide. A practical upper limit to the concentration of hydrogen in the treating gases results from certain process constraints. These practical constraints include the requirement that while hydrogen reactive gas concentrations and volumes favor the production of iron carbide as shown by kinetic studies, the increasingly higher cost and diminishing benefit of increasing pressure to increase total hydrogen volumes at high pressures limits the use of increased pressure as a method of increasing reactive gas concentrations and volumes.

One way to increase the quantity of hydrogen in the reactor is to increase the system pressure, thereby generally resulting in more gas, including hydrogen gas, per actual unit volume of flow. An increase in pressure could be effected, for example, by increasing the feed rate of hydrogen, or another gas component, into the system.

Although, intuitively, the concentration of hydrogen would seem to increase with ever increasing pressure, such is not necessarily the case due to equilibrium conditions within the reactor between individual gases in the reaction gas mixture. Thus, in the reaction gas mixture comprising hydrogen, methane, water, carbon monoxide, and carbon dioxide, methane in the mixture becomes more stable at higher pressures and the equilibrium concentration of hydrogen relative to methane is shifted to favor a higher volume fraction of methane and a lower volume fraction of hydrogen in the reaction gas mixture. Thus, it is possible that with increasing pressures, the gas mixture could become deficient in hydrogen and a loss of production could result even though the gas mixture is still suitable for the production of iron carbide.

Another way of increasing hydrogen concentration is to increase the temperature within the reactor. Methane becomes less stable at higher temperatures and the equilibrium concentration of hydrogen relative to methane tends to increase, thereby increasing the volume fraction of hydrogen and decreasing the volume fraction of methane in the reaction gas mixture.

However, if temperatures become too high, reaction kinetics can be detrimentally affected and the rate of conversion of reactor feed to iron carbide can be reduced, even though the concentration of hydrogen might be increased.

A combination of temperature and pressure changes can be utilized to affect the hydrogen concentration and improve the rate of production of iron carbide. However, certain combinations of higher temperature and higher pressure that could result in a reduced rate of iron carbide production should be avoided.

Although the effect of temperature on reaction kinetics for the conversion of reactor feed to iron carbide depends to some degree on the pressure, generally, temperatures from about 400° C. to about 700° C. are preferred. More preferably, the temperature is from about 500° C. to about 650° C., even more preferably from about 525° C. to about 610° C. and most preferably from about 570° C. to about 600° C.

In one embodiment of the present invention, the rate of iron carbide production is controlled by control of temperature and pressure in the reactor. The temperature is preferably maintained from about 400° C. to about 700° C., more preferably from about 500° C. to about 650° C., and even more preferably from about 525° C. to about 610° C., and most preferably from about 570° C. to about 600° C. to ensure that reaction kinetics are not impaired by temperatures that are too high or too low. Generally, temperatures near the higher end of the preferred ranges are more preferred since hydrogen concentrations tend to be higher at higher temperatures. One particularly preferred temperature range is from about 580° C. to about 600° C., and especially a temperature of about 590° C.

Relative concentrations, generally represented by volume fractions, of individual gases in the reactor must be maintained within the range suitable for production of iron carbide, as previously discussed. The pressure in the reactor, however, is generally increased to increase the volume of hydrogen per unit of time in the reaction vessel and thereby improve the rate of production of iron carbide. As pressure in the system is increased, however, a pressure will be reached for any given temperature at which the volume fraction of hydrogen in the reaction gas mixture begins to decrease with further increases in pressure. It has been found that iron carbide can be produced at an efficient rate by operating at a pressure from slightly above to slightly below the pressure at which the volume fraction of hydrogen begins to decrease with increasing pressure. Preferably the pressure is maintained at from about one atmosphere above to about one atmosphere below, and more preferably from about 0.5 atmosphere above to about 0.5 atmosphere below, the pressure at which the volume fraction of hydrogen begins to decrease at a given operating temperature.

Concentration, as used herein, is generally represented by the partial pressure of an individual gas specie. Partial pressure is generally calculated as the volume fraction of a gas specie multiplied by the total system pressure, on an absolute basis. Relative concentration of a gas specie, however, is generally represented by the volume fraction, or volume percentage, of the gas specie in the reaction gas mixture. It will be understood that the concentration of a gas can increase with increasing pressure even though the relative concentration, or volume fraction, of the gas decreases.

In one embodiment, system pressures from about 3 atmospheres to about 5 atmospheres, absolute, are preferred to result in suitably high rates of iron carbide production according to the present invention. More preferably, the pressure is from about 3.5 atmospheres to about 4.5 atmospheres. A pressure of around 4 atmospheres is often very desirable.

It has been surprisingly found that certain combinations of narrow temperature ranges and higher pressures result in very efficient iron carbide production. In one preferred embodiment, the temperature is maintained from about 525° C. to about 610° C., and more preferably from about 570° C. to about 600° C., and the pressure is maintained from about 3 atmospheres to about 5 atmospheres. Even more preferably, the temperature is maintained from about 580° C. to about 600° C. and the pressure is maintained from about 3.5 atmospheres to about 4.5 atmospheres. Particularly preferred is a temperature of about 590° C. and a pressure of about 4 atmospheres.

In another embodiment the temperature is maintained within a preferred range, as previously discussed, and pressure is increased to increase hydrogen flows, to improve the rate of conversion of reactor feed to iron carbide. Generally, pressure can be increased to a point where further increases in pressure would result in a percentage increase in total gas flow that is less than the reduction in the volume percentage of hydrogen in the reaction gas mixture, which occurs above the pressure at which hydrogen attains a maximum volume fraction at the temperature of interest, as previously described.

The pressure of operation is also affected practically by local economics for the production of iron carbide. For example, currently, iron carbide produced by the present invention will be most competitive with recycle steel scrap. Maintaining a shorter conversion time in the production of iron carbide according to the invention is economically necessary in the United States, for example, where recycle steel scrap prices are currently about $90 per ton and labor rates are high. By contrast, a longer conversion time might be economically satisfactory in India, where scrap prices are in excess of $200 per ton and labor rates are low.

In one embodiment, greater than about 90 percent, and preferably greater than about 95 percent of iron in the reactor feed is converted to iron carbide with a reactor retention time for reactor feed of less than about 35 hours. Such conversion times would require, for example, treating the reactor feed with greater than about 1.1 moles of total treating gas per hour per mole of iron at a temperature from about 580° C. to about 600° C. More preferably, said conversion is accomplished with a retention time for reactor feed of less than about 20 hours, and even more preferably from about 15 to about 18 hours. Such conversion would require, for example, greater than about 2.0 moles of total treating gas per hour per mole of iron at a temperature from about 580° C. to about 600° C. Very short conversion times are also possible, although such fast conversion is usually not practical due to excessive equipment and process operational costs. For example, greater than about 90 percent conversion is possible with a reactor feed retention time of less than about 5.5 hours using total treating gas of greater than about 7.4 moles of treating gas per hour per mole of iron at a temperature from about 580° C. to about 600° C.

While various embodiments of the invention have been discussed, it will be appreciated by those skilled in the art that various modifications and variations are possible, without departing from the spirit and scope of the invention, as defined by the claims.

What is claimed is:

1. A process for converting iron-containing reactor feed to a product comprising iron carbide, the process comprising the steps of:
   (a) inputting to a reactor an iron-containing reactor feed;
   (b) contacting said reactor feed in said reactor with a gas mixture comprising a reducing gas and a carburizing gas;
   (c) determining temperature, pressure, and relative concentrations of gases in said reactor;
   (d) generating a phase stability diagram using said determined temperature and relative concentration of gases and determining from said phase stability diagram whether said temperature and relative gas concentrations in said reactor are suitable for converting reactor feed into iron carbide;
   (e) adjusting as necessary to provide for conversion of said reactor feed into iron carbide at least one process parameter selected from the group of process parameters consisting of reactor temperature, reactor pressure, relative gas concentrations in said reactor and combinations thereof;
   (f) evaluating whether the rate of conversion of reactor feed into iron carbide is acceptable;
   (g) changing as necessary at least one parameter selected from the group of parameters consisting of reactor temperature, reactor pressure, and relative gas concentrations in said reactor and combinations thereof to convert reactor feed into iron carbide at an acceptable rate;
   (h) repeating steps (c) through (g) as necessary until the conditions of temperature, pressure and relative gas concentrations in the reactor are suitable for conversion of reactor feed to iron carbide at an acceptable rate; and
   (i) converting at least a portion of said reactor feed into iron carbide.

2. The process of claim 1, wherein said carburizing gas comprises methane and said reducing gas comprises hydrogen.

3. The process of claim 1, wherein said determining relative gas concentrations in said reactor in step (c) comprises measuring the concentrations of at least two separate gas components by at least two different measurement techniques.

4. The process of claim 1, wherein said gases for which relative gas concentrations are determined in step (c) comprise each of hydrogen, methane, water, carbon dioxide, and carbon monoxide.

5. The process of claim 1, wherein an exiting gas stream exits said reactor, said exiting gas stream comprising water, and wherein said determining relative gas concentrations in said reactor step (c) comprises removing at least some of the water from said exiting gas stream, measuring the relative concentrations of individual gases in said dewatered exiting gas stream, determining the concentration of said individual gases on a dry basis, and converting said dry basis concentrations to wet basis concentrations at reactor conditions, said exiting gas stream comprising each of hydrogen, methane, water, carbon dioxide, and carbon monoxide.

6. The process of claim 1, wherein said reactor feed comprises iron oxide.

7. The process of claim 1, further comprising removing at least some water from a gas stream exiting said reactor and cycling for input into said reactor at least a portion of said dewatered gas stream exiting said reactor.

8. A process for converting iron-containing feed to a product comprising iron carbide, the process comprising the steps of:
(a) inputting to a reactor an iron-containing reactor feed;
(b) contacting said reactor feed in said reactor with a gas mixture comprising a reducing gas and a carburizing gas at a pressure from about 3 atmospheres absolute to about 5 atmospheres absolute;
(c) evaluating whether the rate of conversion of reactor feed into iron carbide is acceptable; and
(d) adjusting as necessary reactor pressure to convert reactor feed into iron carbide at an acceptable rate; and
(e) converting at least a portion of said reactor feed to iron carbide at an acceptable rate.

9. The process of claim 8, further comprising removing at least some water from a gas stream exiting said reactor such that water in the exiting gas stream is reduced to an acceptable level for input into the reactor, and inputting into said reactor at least a portion of said dewatered gas stream exiting said reactor.

10. A process for converting iron-containing reactor feed to a product comprising iron carbide, the process comprising the steps of:
(a) inputting to a reactor an iron-containing reactor feed;
(b) contacting said reactor feed in said reactor with a gas mixture comprising a reducing gas and a carburizing gas, said reducing gas comprising hydrogen and said carburizing gas comprising gas selected from the group consisting of methane and carbon monoxide, said contacting at a temperature of from about 525° C. to about 610° C. and a pressure from about 3 atmospheres absolute to about 5 atmospheres absolute;
(c) converting at least a portion of said reactor feed into iron carbide.

11. The process of claim 10, wherein said contacting is at a temperature of from about 580° C. to about 600° C.

12. The process of claim 10, wherein said contacting is at a pressure from about 3.5 atmospheres absolute to about 4.5 atmospheres absolute.

13. The process of claim 10, wherein said gas mixture comprises hydrogen, methane, water, carbon monoxide and carbon dioxide.

14. The process of claim 10, further comprising the steps of generating a phase stability diagram for conditions of temperature, pressure and gas compositions in the reactor, determining from said phase stability diagram whether conditions of temperature, pressure and gas concentrations in the reactor are suitable for converting reactor feed into iron carbide, and adjusting as necessary at least one parameter selected from the group consisting of reactor temperature, reactor pressure, and gas compositions in the reactor to convert reactor feed into iron carbide.

15. A process for converting iron-containing reactor feed to a product comprising iron carbide, the process comprising the steps of:
(a) inputting to a reactor an iron-containing reactor feed;
(b) contacting said reactor feed in said reactor with a gas mixture comprising a reducing gas and a carburizing gas, said reducing gas comprising hydrogen and said carburizing gas comprising gas selected from the group consisting of methane, carbon dioxide, carbon monoxide, and combinations thereof;
(c) determining a pressure above which the volume fraction of hydrogen gas in said reactor would decrease at constant temperature; and
(d) converting at least a portion of said reactor feed into iron carbide at a reactor pressure from about one atmosphere absolute below to about one atmosphere absolute above the pressure determined in step (c).

16. The process of claim 15, wherein said converting is at a reactor pressure from about 0.5 atmosphere absolute below to about 0.5 atmosphere absolute above the pressure determined in step (c).

17. The process of claim 15, wherein said converting is at a temperature of from about 570° C. to about 600° C.

18. A process for converting iron-containing reactor feed to a product comprising iron carbide in a fluidized bed reactor, the process comprising the steps of:
(a) first monitoring of gas concentrations for at least two individual gases in a region substantially adjacent to the fluidized bed;
(b) second monitoring of gas concentrations of said at least two individual gases using a different technique than the technique used in said first monitoring;
(c) comparing said first monitored and said second monitored gas concentrations and alerting an operator if said first and second monitored concentrations are incompatible;
(d) determining temperature and pressure in the reactor;
(e) determining concentrations of gases in the reactor;
(f) evaluating whether the conditions of temperature, pressure and gas compositions are suitable for converting reactor feed into iron carbide;
(g) adjusting as necessary at least one parameter selected from the group consisting of reactor temperature, reactor pressure, concentrations of gases in said reactor and combinations thereof to provide for the conversion of reactor feed into iron carbide; and
(h) converting at least a portion of said reactor feed into iron carbide.

19. A process for converting iron-containing reactor feed to a product comprising iron carbide, the process comprising the steps of:
(a) inputting to a reactor an iron-containing reactor feed;
(b) contacting said reactor feed with a gas mixture comprising a reducing gas and a carburizing gas;
(c) removing at least some water from gases exiting said reactor;
(d) determining concentrations of said exiting gases on a dry basis;
(e) converting said dry basis concentrations to wet basis concentrations at reactor conditions;
(f) generating a stability phase diagram comprising the phases of $Fe_3O_4$, $FeO$, $Fe$ and $Fe_3C$;
(g) determining from said stability phase diagram whether the reactor conditions of temperature, pressure, and gas concentrations are suitable for production of iron carbide from said reactor feed;
(h) adjusting as necessary at least one parameter selected from the group consisting of reactor temperature, reactor pressure, gas concentrations in the reactor and combinations thereof, taking into account the interdependence of said parameters, to provide for conversion of said reactor feed into iron carbide; and (i) converting at least a portion of said reactor feed into iron carbide.

20. A process for converting iron-containing reactor feed to a product comprising iron carbide, the process comprising the steps of:

(a) inputting to a reactor an iron-containing reactor feed;

(b) contacting said reactor feed in said reactor with a gas mixture comprising hydrogen, methane, water, carbon dioxide, and carbon monoxide; and (c) converting at least a portion of said reactor feed into iron carbide with a retention time in said reactor of less than about 20 hours at a reactor pressure from about 3 atmospheres absolute to about 5 atmospheres absolute and a reactor temperature from about 570° C. to about 600° C.

* * * * *